United States Patent [19]

Kong et al.

[11] Patent Number: 5,427,747
[45] Date of Patent: Jun. 27, 1995

[54] METHOD AND APPARATUS FOR PRODUCING OXYGENATES FROM HYDROCARBONS

[75] Inventors: Peter C. Kong; Paul A. Lessing, both of Idaho Falls, Id.

[73] Assignee: Lockheed Idaho Technologies Company, Idaho Falls, Id.

[21] Appl. No.: 255,603

[22] Filed: Jun. 8, 1994

[51] Int. Cl.$^6$ .............................................. C01B 13/00
[52] U.S. Cl. ................. 422/186; 422/186.04; 422/906
[58] Field of Search ................... 422/186, 186.04, 906, 422/907

[56] References Cited

U.S. PATENT DOCUMENTS

| | | | |
|---|---|---|---|
| 4,774,062 | 9/1988 | Heinemann | 422/186.19 |
| 4,954,320 | 9/1990 | Birmingham et al. | 422/186.04 |
| 4,956,152 | 9/1990 | Keough et al. | 422/181 |
| 4,966,666 | 10/1990 | Waltonen | 204/164 |
| 5,026,484 | 6/1991 | Juvan | 210/717 |
| 5,061,462 | 10/1991 | Suzuki | 422/186.04 |
| 5,102,629 | 4/1992 | Hayashi et al. | 422/186.18 |
| 5,236,672 | 8/1993 | Nunez et al. | 422/186.04 |

OTHER PUBLICATIONS

Iwahara, H. et al.; *Solid State Ionics 9 & 10*, 1021–1026 (1983).
Steele, B. C. H., et al.; *Solid State Ionics 28–30*; 1547–1552 (1988).
Cook F. L., et al. *Proc. of 3rd Annual DOE Fuel Cell Contractors Mtg.*, (1991).
Tai, L. W. et al.; *J. Am Ceram. Soc.*, 74 [3] 501–504 (1991).
McCulla, W. H., et al. "Treatment of Hazardous Organic Wastes Using Wet Air Plasma Oxidation", *Plasma Applications to Waste Treatment, 1st INEL Plasma Waste Workshop*, paper III-3 (1991).
Neely W. C. et al.; "Decomposition of Organic Compounds by Silent Discharge Plasma", *Plasma Applications to Waste Treatment, 1st INEL Plasma Waster Workshop*, paper IV-3 (1991).
Higashi, M. et al.; *IEEE Trans. on Plasma Science*, 20 [1], 1–12 (1992).
Shepelev, S. S. et al.; to be published in *Plasma Chemistry and Plasma Processing*.
Iwahara, H., et al.; *Electrochem. Soc. 135*, [2] 529–533 (1988).
Kharas, K. C. C. et al.; *J. Amer. Chem. Soc.*, 2336 (1989).
Woldman, L. S. et al.; *Catalysis Letters 8* 61–66 (1991).
Jacobson, A. J., et al. *Chemistry of Electronic Ceramic Materials*, NIST Special Publication 804, 151–161 (1990).
Pujare, N. U. et al.; *J. Electrochem. Soc.*, 135, 2544 (1989).
Seimanides, S. et al.; *J. Electrochem Soc.*, 133, 1535 (1986).
Mar'ina, O. A. et al.; *Mat. Sci. and Eng.*, B13, 153–155 (1992).
Vayenas, C. G., et al.; *Nature*, 343, 625 (1990).
Otsuka, K. et al.; *Catalysis Letters*, 1, 423 (1988).

*Primary Examiner*—Donald P. Walsh
*Assistant Examiner*—Daniel Jenkins
*Attorney, Agent, or Firm*—Wells, St. John, Roberts, Gregory & Matkin

[57] ABSTRACT

A chemical reactor for oxygenating hydrocarbons includes: a) a dielectric barrier discharge plasma cell, the plasma cell comprising a pair of electrodes having a dielectric material and void therebetween, the plasma cell comprising a hydrocarbon gas inlet feeding to the void; b) a solid oxide electrochemical cell, the electrochemical cell comprising a solid oxide electrolyte positioned between a porous cathode and a porous anode, an oxygen containing gas inlet stream feeding to the porous cathode side of the electrochemical cell; c) a first gas passageway feeding from the void to the anode side of the electrochemical cell; and d) a gas outlet feeding from the anode side of the electrochemical cell to expel reaction products from the chemical reactor. A method of oxygenating hydrocarbons is also disclosed.

16 Claims, 3 Drawing Sheets

METHOD AND APPARATUS FOR PRODUCING OXYGENATES FROM HYDROCARBONS

CONTRACTUAL ORIGIN OF THE INVENTION

The United States Government has rights in this invention pursuant to Contract No. DE-AC07-76IDO1570 between the United States Department of Energy and EG&G Idaho, Inc.

TECHNICAL FIELD

This invention relates to methods of oxygenating hydrocarbons and to chemical reactor design for the oxygenation of hydrocarbons.

BACKGROUND OF THE INVENTION

Methane is an abundant hydrocarbon fuel and chemical feed stock, and is expected to remain so for quite some time. It is desirable to upgrade available methane to methyl or higher oxygen atom containing hydrocarbons, such as alcohols, ethers, aldehydes, etc. Existing technologies for converting methane to methanol include destruction of methane to form a synthesis gas ($H_2$ and $CO$), followed by indirect liquefaction steps.

However, conventional catalytic approaches to produce methanol from methane typically have poor conversion efficiencies 18 (25% max.), slow reaction rates, and are not economically competitive because they are typical so energy intensive. One such process, the oxidative coupling process, involves the use of an oxidant to abstract hydrogen from methane and coupling two or more hydrocarbon radicals to form light olefin, oxygenates, and other hydrocarbons. The oxidants are oxygen, halogens and reducible metal oxides as oxygen carriers and catalysts. In the oxidative coupling processes, hydrogen abstraction at the oxygen centers of the catalyst is typically the rate determining step, and catalyst properties are important for end product selectivity. Therefore, the maximum rate of product conversion strongly depends on the rate of radical formation on the active oxygen centers. In order to increase the rates, chemists have used high temperatures, even in excess of 900° C. However, this undesirably promotes deep oxidation of methane to fully oxidized species, such as $CO_2$.

In another strategy, a high temperature dehydrogenation coupling process has a very high radical generation rate, and correspondingly a high rate of light olefin formation. However, the process is plagued by solid carbon formation which lowers the efficiency of the olefin production, and excess hydrogen is necessary to suppress the solid carbon formation.

It would be desirable to enhance the rate of methane activation for conversion to liquid oxygenated hydrocarbons.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the invention, a method of oxygenating hydrocarbons comprises the following steps:

subjecting a gaseous hydrocarbon to a dielectric barrier discharge plasma effective to produce hydrocarbon radicals;

feeding the hydrocarbon radicals to a porous anode side of an electrochemical cell, the electrochemical cell comprising a solid oxide electrolyte positioned between a porous cathode and a porous anode;

feeding a gaseous oxygen containing species to the porous cathode side of the electrochemical cell and generating oxygen containing anions therefrom;

electrochemically driving oxygen containing anions through the solid oxide electrolyte and into the porous anode to provide a reactive oxygen containing species at the porous anode; and reacting the reactive oxygen containing species with the hydrocarbon radicals at the anode to form gaseous oxygenated hydrocarbons.

In accordance with another aspect of the invention, a chemical reactor for oxygenating hydrocarbons comprises:

a dielectric barrier discharge plasma cell, the plasma cell comprising a pair of electrodes having a dielectric material and void therebetween, the plasma cell comprising a hydrocarbon gas inlet feeding to the void;

a solid oxide electrochemical cell, the electrochemical cell comprising a solid oxide electrolyte positioned between a porous cathode and a porous anode, an oxygen containing gas inlet stream feeding to the porous cathode side of the electrochemical cell;

a first gas passageway feeding from the void to the anode side of the electrochemical cell; and a gas outlet feeding from the anode side of the electrochemical cell to expel reaction products from the chemical reactor.

Figure 1:
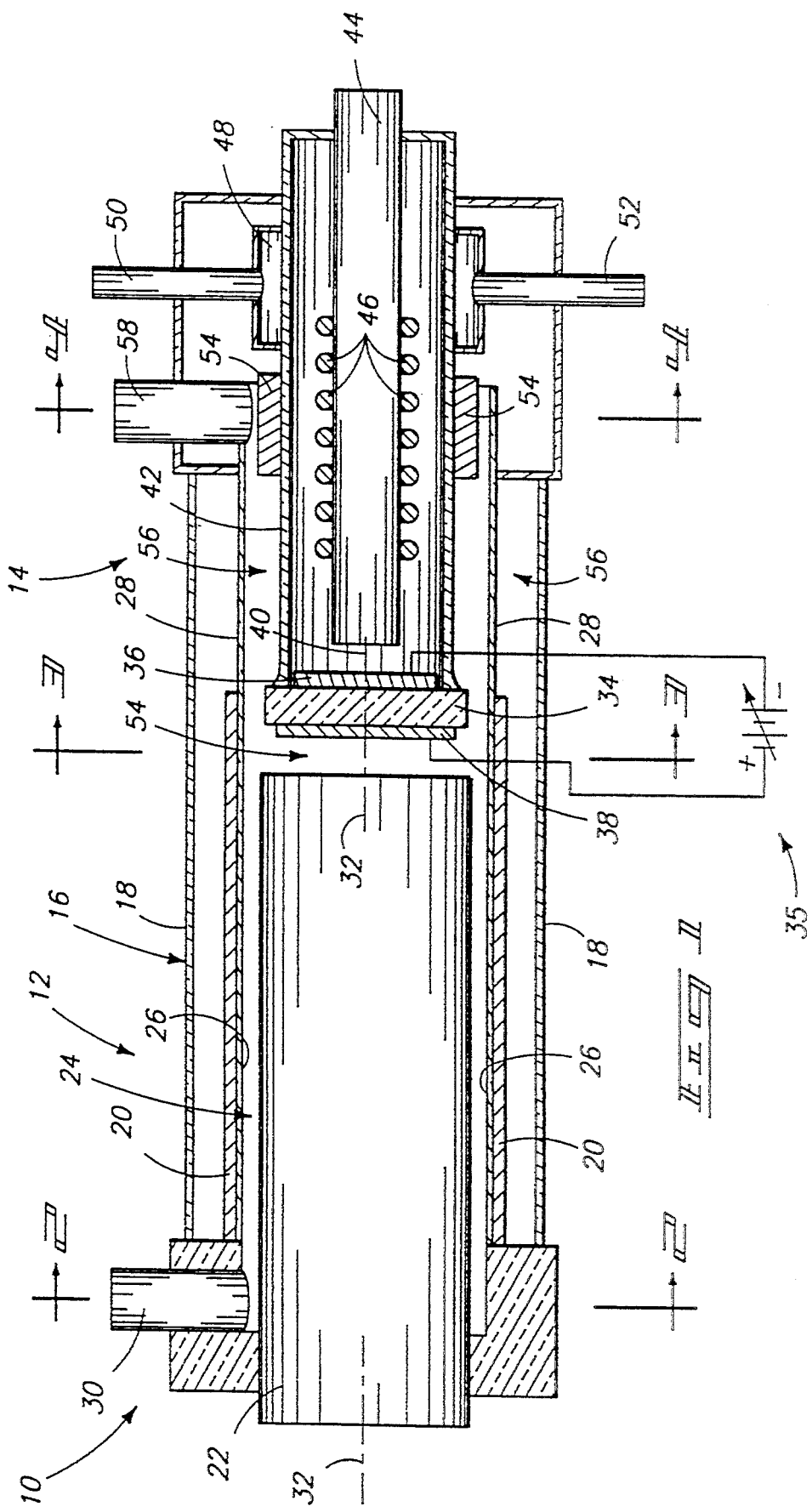
FIG. 1 is a diagrammatic cross sectional view of a chemical reactor designed for oxygenation of hydrocarbons in accordance with the invention.
Figure 2:
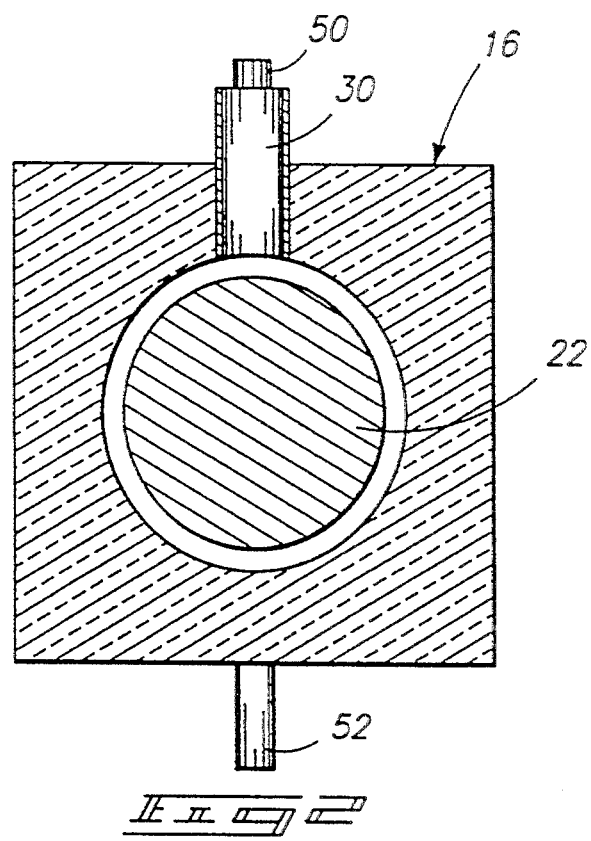
FIG. 2 is a section view of the FIG. 1 apparatus taken along line 2—2 of FIG. 1.
Figure 3:
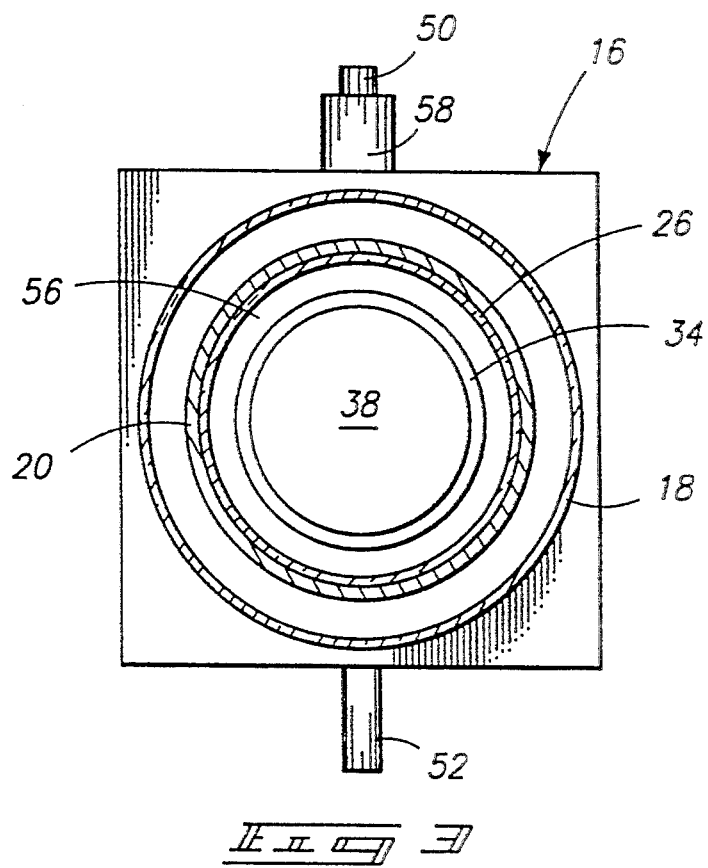
FIG. 3 is a sectional view of the FIG. 1 apparatus taken through line 3—3 in FIG. 1.
Figure 4:
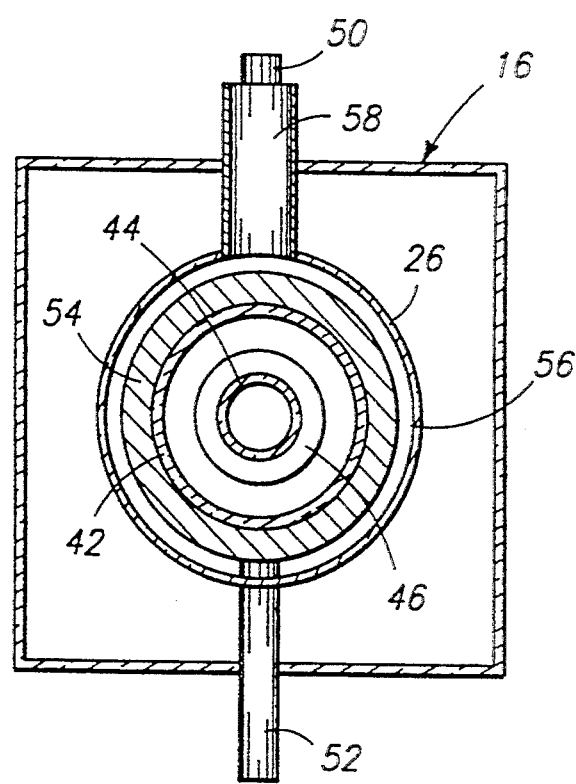
FIG. 4 is a sectional view of the FIG. 1 apparatus taken through line 4—4 of FIG. 1.

More specifically with reference to FIGS. 1–4, a chemical reactor for oxygenating hydrocarbons is indicated generally with reference numeral 10. Such comprises a longitudinally elongated dielectric barrier discharge plasma cell 12 and a solid oxide electrochemical cell 14. Cells 12 and 14 are enclosed and supported within a common housing 16. For purposes of the continuing discussion, housing 16 can be considered as having an exterior 18.

Discharge plasma cell 12 comprises a pair of electrodes 20 and 22. A layer 26 of dielectric material and a void 24 are positionally between electrodes 20 and 22. Electrode 20 is in the form of an elongated metal cylindrical screen shell. One example material of construction would be a stainless steel. Electrode 22 is in the form of an elongated rod member (solid or hollow) which is received concentrically internal of cylindrical shell electrode 20. One example material of construction for such a central electrode would be a stainless steel. Dielectric barrier layer 26 would preferably be comprised of a ceramic oxide material (i.e., quartz, zirconia, alumina, glass, etc.), and is shown having a longitudinally extending portion 28 which projects longitudinally beyond the illustrated right-end of cylindrical shell electrode 20. Cylindrical shell electrode 20 also extends longitudinally outwardly beyond the right-end of center rod electrode 22.

Electrodes 20 and 22 define void 24 in the shape of an elongated annulus therebetween. A hydrocarbon gas inlet feed 30 extends from exterior of housing 16 to annular void 24. The elongated rod electrode 22 is centrally positioned within shell electrode 20 to define a central axis 32 of dielectric barrier discharge plasma cell 12.

Turning now to solid oxide electrochemical cell 14, it comprises a solid oxide electrolyte 34 positioned between a porous cathode 36 and a porous anode 38. Anode 38, cathode 36 and solid electrolyte 34 are positioned and sandwiched about a common central axis 40. An external electromotive force generator 35, such as a variable voltage battery or generator, is provided to complete the electrolytic circuit. Such can be utilized to enhance the driving of anions through the electrolyte, as is described below. An elongated ceramic shell 42 extends rearwardly (to the right) from solid electrolyte 34 and encompasses cathode 36 therewithin. An inner elongated concentric gas inlet stream or tube 44 is provided for feeding oxygen containing gas from exteriorly of housing 16 to the porous cathode side of the anode 38/electrolyte 34/cathode 36 composite. Tube 44 is surrounded by a plurality of electric heating elements 46 for maintaining oxygen containing gas within tube 44 at a desired temperature and in a desired vaporized condition.

An encircling water jacket/ring 48 surrounds a portion of shell 42. Water is fed to jacket 48 via a stream 50 and out from jacket 48 via a stream 52, thus providing desired cooling of shell 42. An annular supporting ring 54 surrounds tube 42 to position the anode side of the electrochemical cell cathode 36/electrolyte 34/anode 38 composite in axial juxtaposition to elongated rod member electrode 22, with discharge plasma cell central axis 32 and common axis 40 being in end-to-end alignment. Such also effectively provides cylindrical shell electrode 20 to extend longitudinally over and beyond porous anode 38 and over solid electrolyte 34.

The described arrangement defines a first passageway or void 54 which feeds from annulus 24 to porous anode 38. A second gas passageway 56 is annularly formed about tube 42 and oxygen containing gas inlet stream 44, and feeds from first passageway 54 and the anode side of electrochemical cell 14. Second gas passageway 56 feeds to a gas outlet 58 to expel reaction products from chemical reactor 10. Accordingly, gas outlet 58 extends to externally of housing 18.

Operation

A method of operating the above apparatus in accordance with the invention would be to provide a gaseous hydrocarbon feed, such as methane, to and through inlet 30 into annular passageway 24. The gas flowing therethrough would be subjected to a dielectric barrier discharge between electrodes 20 and 22. A dielectric barrier discharge is a non-equilibrium or "cold" plasma in which the electron temperature is typically very high (i.e., $10^{4°}$ K.), while the gas temperature remains at ambient (i.e., less than 373° K.). Specifically, when a high voltage (i.e., 1000 or greater AC/DC volts) is applied between metal electrodes 20 and 22, the dielectric barrier formed by layer 26 effectively breaks down, enabling multiple discharges to be maintained between dielectric barrier 26 and central electrode 22. The discharges are in the form of micro-arcs which induce dissociation and ionization of gases. The dissociation of gases in this type of discharge device will generate a high concentration of free radicals, in the plasma state, which are reactive at high rates.

An example operable voltage and current for dielectric discharge plasma cell 12 would be upward of 1000 V and, 10 to 100 mA, respectively, Under preferred conditions, dielectric discharge plasma cell 12 would be operated at ambient room temperatures, with the gases flowing thereto being heated to approximately 100° C. or greater as a result from operation of solid oxide electrochemical cell 14, as is described in more detail below. The discharges are effective to generate the radicals and cause partial hydrogen abstraction from the hydrocarbon molecules, such as the difficult to cleave C—H bond in methane.

Radicals formed within annulus 24 are caused to flow inwardly to passageway 54 and in close proximity and into porous anode 38 by the subsequent flow of more gas injected into inlet 30. Accordingly, reactive hydrocarbon radicals are presented at porous anode 38. The outer cylindrical shell electrode 20 preferably extends beyond the inner end terminus of central electrode 22, as described above, to enable arcing and radical generation even beyond the inner right-end terminus of center electrode 22 within passageway 54.

The solid oxide electrochemical cell would also be operated in unison with operation of the dielectric barrier discharge plasma cell 12. Specifically, a gaseous oxygen containing species would be fed to the porous cathode side of electrochemical cell 14. Example and preferred materials would be steam, $H_2O_2$ and/or $O_2$. Heating elements 46 are provided to maintain steam in a vapor condition while being supplied to porous cathode 36. The gaseous oxygen containing species is converted to oxygen containing anions at cathode 36. These anions are electrochemically driven through the electrolyte membrane and discharge at and through anode 38 to provide a reactive oxygen containing species at the anode. The anion driving can be enhanced by the providing an external driving force with circuit 35.

The reactive species will typically be in the form of the driven anions or oxygen containing radicals generated therefrom. Most preferably, a reaction enhancing electrocatalytic effect is provided by the electrochemical cell. For example in such instance, the material of the anode or the material of the solid electrolyte constitute catalytic sites. These catalytic sites significantly enhance the overall reaction by converting the driven anions into radicals or other activated species which react with the hydrocarbon radicals.

Thus, highly reactive oxygen containing species capable of reaction with hydrocarbon radicals are presented at porous anode 38 from the operation of cell 14. There, the hydrocarbon radicals formed by the dielectric discharges combine with the oxygen anions, radicals and/or other activated species to form liquid fuels in the form of gaseous oxygenated hydrocarbons, such as methyl alcohol. The oxygenated hydrocarbons would then flow through second passageway 56 to a product outlet stream 58.

The rate of oxidants supplied to anode 38 would be controlled via external circuit 35 (controlled power supply regulates the voltage and current) that conducts excess electrons out of the anode. For example, the ion flux through solid electrolyte 34 can be increased by application of a DC potential (i.e., an external electromotive force) across the electrodes. Control of the current flow (directly related to ion flux across solid electrolyte 34) can be established either by an external resistor for the case of no external DC potential or by a variable voltage supply if a greater flow is desired. Depending upon rate of reaction, the partial oxidation could be self-sustaining or even produce excess heat or electrical power. An example temperature operating range for cell 14 is from 100° C. to 600° C.

Because the amount of oxidant radicals supplied to anode 38 can be finely controlled, higher overall conversions to methanol at a fast methane input flow rate can be gained. This is because the system is not limited by long residence times or oxygen availability, since reactive oxygen is generated by purely electrochemical means or most preferably by a combination of electrochemical and electrocatalytic means. Ambient temperature operation of the dielectric barrier discharge plasma cell 12 should prevent solid carbon formation during the discharge because complete hydrogen abstraction from the hydrocarbon is not encouraged. Accordingly, there is a correspondingly enhancement in the efficiency of liquid fuel formation.

Numerous possible reactions involved in the dielectric barrier discharge and at the solid oxide electrochemical cell surface are shown below.

Dielectric Barrier Discharge—Hydrocarbon Radical Generation $CH_4 \rightarrow CH_3 + H$
$CH_3 \rightarrow CH_4 + H$
$CH_2 \rightarrow CH + H$
$CH_3 \rightarrow CH_3^+ + e^-$
$CH_2 \rightarrow CH_2^+ + e^-$
$CH \rightarrow CH^+ + e^-$
$CH_3 + CH_2 \rightarrow CH_3CH_2$
and others Solid Oxide Electrochemical Cell—Hydroxyl and Oxygen Anions and Radical Generation At Cathode Surfaces $H_2O \rightarrow OH + H$
$HO + e^- \rightarrow OH^-$
$O_2 \rightarrow 2O$
$2O + 4e^- \rightarrow 2O^{2-}$ At the Anode Surfaces $OH^- \rightarrow e^- + OH$
$2O^{2-} \rightarrow 2O + 4e^-$ Possible Reactions at/near Anode for Alcohol Production Hydroxyl Reactions $CH_3 + OH \rightarrow CH_3OH$
$CH_3CH_2 + OH \rightarrow CH_3CH_2OH$
$CH_3 + OH \rightarrow CH_3O + H$ Proton Reactions $CH_3O + H \rightarrow CH_3OH$
$CH_3CH_2O + H \rightarrow CH_3CH_2OH$ Oxide Reactions $CH_3 + O \rightarrow CH_3O$
$CH_3O + H \rightarrow CH_3OH$ $CH_4 + O \rightarrow CH_3OH$ (not as probable)
and others High ionic conductivity at low to moderate temperature may be a necessary criteria for the material of solid electrolyte 34. Mixed oxide ceramic materials that function at sufficiently low temperatures (i.e., 300°–600° C.) are highly desirable and may be necessary to prevent deep oxidation of hydrocarbons to $CO_2$ etc. Example classes of electrolyte materials operable for such low temperature operation include:

(1) $SrCe_{0.95}Y_{0.05}O_{3-x}$
(2) $BaCe_{0.9}Gd_{0.1}O_3$
(3) $Sr_2Gd_2O_5$
(4) Ion exchanged $\beta''$ alumina It is expected that use of one of the above electrolytes will likely provide the above described desired electrocatalytic effect at the surface of electrolyte 34 exposed to the hydrocarbons that anode 38 may only have to function as a current collector. However, it may also be configured to function as a catalyst as well. The anode material as well may provide a catalytic effect.

The composition for porous anode 38 (i.e., the current collector) will preferably be selected from one of the following compositions:

(1) Silver
(2) Nickel
(3) Doped $CaTiO_3$
(4) $La_{0.85}Sr_{0.15}MnO_3$
(5) $La_{0.85}Sr_{0.15}CrO_3$
(6) platinum The porous cathode 36 would preferably be comprised of a metal screen mesh, such as elemental platinum or elemental silver.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A chemical reactor for oxygenating hydrocarbons comprising:

a dielectric barrier discharge plasma cell, the plasma cell comprising a pair of electrodes having a dielectric material and void therebetween, the plasma cell comprising a hydrocarbon gas inlet feeding to the void;

a solid oxide electrochemical cell connected in fluid communication with the dielectric barrier discharge plasma cell, the electrochemical cell comprising a solid oxide electrolyte positioned between a porous cathode and a porous anode, an oxygen containing gas inlet stream feeding to the porous cathode side of the electrochemical cell;

a first gas passageway providing fluid interconnection between the dielectric barrier discharge plasma cell and the solid oxide electrochemical cell, the first gas passageway fluidically interconnecting the dielectric barrier discharge plasma cell void to the anode side of the electrochemical cell; and a gas outlet feeding from the anode side of the electrochemical cell to expel reaction products from the chemical reactor.

2. The chemical reactor for oxygenating hydrocarbons of claim 1 wherein the dielectric barrier discharge plasma cell and electrochemical cell are enclosed and supported within a common housing, the housing having an exterior, the gas inlets and the gas outlet extending to the housing exterior.

3. The chemical reactor for oxygenating hydrocarbons of claim 1 further comprising a second gas passageway feeding between the anode side of the electrochemical cell and the gas outlet.

4. The chemical reactor for oxygenating hydrocarbons of claim 1 further comprising a second gas passageway feeding between the anode side of the electrochemical cell and the gas outlet, the second gas passageway comprising an elongated annulus formed about the oxygen containing gas inlet stream.

5. The chemical reactor for oxygenating hydrocarbons of claim 1 wherein,
the dielectric barrier discharge plasma cell is longitudinally elongated, one of the pair of electrodes comprising an elongated cylindrical shell, the other of the pair of electrodes comprising an elongated member received concentrically internal of the cylindrical shell, the void comprising an elongated annulus between the shell and member; and
the anode side of the electrochemical cell is positioned in axial juxtaposition to the elongated member electrode.

6. The chemical reactor for oxygenating hydrocarbons of claim 1 wherein,
the dielectric barrier discharge plasma cell is longitudinally elongated, one of the pair of electrodes comprising an elongated cylindrical shell, the other of the pair of electrodes comprising an elongated member received concentrically internal of the cylindrical shell, the void comprising an elongated annulus between the shell and member, the cylindrical shell electrode extending longitudinally beyond the elongated member electrode; and
the anode side of the electrochemical cell is positioned in axial juxtaposition to the elongated member electrode.

7. The chemical reactor for oxygenating hydrocarbons of claim 1 wherein,
the dielectric barrier discharge plasma cell is longitudinally elongated, one of the pair of electrodes comprising an
elongated cylindrical shell, the other of the pair of electrodes comprising an elongated member received concentrically internal of the cylindrical shell, the void comprising an elongated annulus between the shell and member;
the anode side of the electrochemical cell is positioned in axial juxtaposition to the elongated member electrode; and
the cylindrical shell electrode extends longitudinally beyond the elongated member electrode and over the anode.

8. The chemical reactor for oxygenating hydrocarbons of claim 1 wherein,
the dielectric barrier discharge plasma cell is longitudinally elongated, one of the pair of electrodes comprising an elongated cylindrical shell, the other of the pair of electrodes comprising an elongated member received concentrically internal of the cylindrical shell, the void comprising an elongated annulus between the shell and member, the elongated member electrode defining a dielectric barrier discharge plasma cell central axis; and
the anode, cathode and solid electrolyte of the electrochemical cell are positioned about a common central axis, the plasma cell central axis and the common central axis being in end-to-end alignment.

9. The chemical reactor for oxygenating hydrocarbons of claim 1 wherein the dielectric barrier discharge plasma cell and electrochemical cell are enclosed and supported within a common housing, the housing having an exterior, the gas inlets and the gas outlet extending to the housing exterior; and
further comprising a second gas passageway feeding between the anode side of the electrochemical cell and the gas outlet.

10. The chemical reactor for oxygenating hydrocarbons of claim 1 wherein the dielectric barrier discharge plasma cell and electrochemical cell are enclosed and supported within a common housing, the housing having an exterior, the gas inlets and the gas outlet extending to the housing exterior; and
further comprising a second gas passageway feeding between the anode side of the electrochemical cell and the gas outlet, the second gas passageway comprising an elongated annulus formed about the oxygen containing gas inlet stream.

11. The chemical reactor for oxygenating hydrocarbons of claim 1 wherein,
the dielectric barrier discharge plasma cell is longitudinally elongated, one of the pair of electrodes comprising an elongated cylindrical shell, the other of the pair of electrodes comprising an elongated member received concentrically internal of the cylindrical shell, the void comprising an elongated annulus between the shell and member, the elongated member electrode defining a dielectric barrier discharge plasma cell central axis, the cylindrical shell electrode extending longitudinally beyond the elongated member electrode; and
the anode, cathode and solid electrolyte of the electrochemical cell are positioned about a common central axis, the plasma cell central axis and the common central axis being in end-to-end alignment.

12. The chemical reactor for oxygenating hydrocarbons of claim 1 wherein,
the dielectric barrier discharge plasma cell is longitudinally elongated, one of the pair of electrodes comprising an elongated cylindrical shell, the other of the pair of electrodes comprising an elongated member received concentrically internal of the cylindrical shell, the void comprising an elongated annulus between the shell and member, the elongated member electrode defining dielectric barrier discharge plasma cell central axis;
the anode, cathode and solid electrolyte of the electrochemical cell are positioned about a common central axis, the plasma cell central axis and the common central axis being in end-to-end alignment; and
the cylindrical shell electrode extends longitudinally beyond the elongated member electrode and over the anode.

13. The chemical reactor for oxygenating hydrocarbons of claim 1 wherein, the dielectric barrier discharge plasma cell is longitudinally elongated, one of the pair of electrodes comprising an elongated cylindrical shell, the other of the pair of electrodes comprising an elongated member received concentrically internal of the cylindrical shell, the void comprising an elongated annulus between the shell and member, the elongated member electrode defining dielectric barrier discharge plasma cell central axis;

the anode, cathode and solid electrolyte of the electrochemical cell are positioned about a common central axis, the plasma cell central axis and the common central axis being in end-to-end alignment;

the cylindrical shell electrode extends longitudinally beyond the elongated member electrode and over the anode; and the dielectric barrier discharge plasma cell and electrochemical cell are enclosed and supported within a common housing, the housing having an exterior, the gas inlets and the gas outlet extending to the housing exterior.

14. A chemical reactor for oxygenating hydrocarbons comprising:

a longitudinally elongated support housing having a housing exterior;

a longitudinally elongated dielectric barrier discharge plasma cell supported within the housing, the plasma cell comprising a pair of electrodes having a dielectric material and void therebetween, one of the pair of electrodes comprising an elongated cylindrical shell, the other of the pair of electrodes comprising an elongated member received concentrically internal of the cylindrical shell, the void comprising an elongated annulus between the shell and member, the elongated member electrode defining a dielectric barrier discharge plasma cell central axis, the plasma cell comprising a hydrocarbon gas inlet feeding from exteriorly of the housing to the void;

a solid oxide electrochemical cell supported within the housing, the electrochemical cell comprising a solid oxide electrolyte positioned between a porous cathode and a porous anode; the anode, cathode and solid electrolyte of the electrochemical cell being positioned about a common central axis; the plasma cell central axis and the common central axis being in end-to-end alignment; an oxygen containing gas inlet stream feeding from exteriorly of the housing to the porous cathode side of the electrochemical cell;

a first gas passageway feeding from the annulus to the anode side of the electrochemical cell;

a second gas passageway annularly formed about the oxygen containing gas inlet stream and feeding from the anode side of the electrochemical cell; and a gas outlet feeding from the second gas passageway to externally of the housing to expel reaction products from the chemical reactor.

15. The chemical reactor for oxygenating hydrocarbons of claim 14 wherein the cylindrical shell electrode extends longitudinally beyond the elongated member electrode.

16. The chemical reactor for oxygenating hydrocarbons of claim 14 wherein the cylindrical shell electrode extends longitudinally beyond the elongated member electrode and over the anode.

* * * * *